(12) United States Patent
Duan et al.

(10) Patent No.: US 9,012,882 B2
(45) Date of Patent: Apr. 21, 2015

(54) GRAPHENE NANOMESH AND METHOD OF MAKING THE SAME

(75) Inventors: Xiangfeng Duan, Los Angeles, CA (US); Yu Huang, Los Angeles, CA (US); Jingwei Bai, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/576,519

(22) PCT Filed: Jan. 28, 2011

(86) PCT No.: PCT/US2011/023002
§ 371 (c)(1),
(2), (4) Date: Aug. 1, 2012

(87) PCT Pub. No.: WO2011/094597
PCT Pub. Date: Aug. 4, 2011

(65) Prior Publication Data
US 2012/0301953 A1 Nov. 29, 2012

Related U.S. Application Data

(60) Provisional application No. 61/300,398, filed on Feb. 1, 2010.

(51) Int. Cl.
*H01L 21/02* (2006.01)
*H01L 29/66* (2006.01)
(Continued)

(52) U.S. Cl.
CPC ........... *H01L 29/78684* (2013.01); *B82Y 30/00* (2013.01); *B82Y 40/00* (2013.01);
(Continued)

(58) Field of Classification Search
CPC .... B82Y 30/00; B82Y 40/00; H01L 29/1606; H01L 21/0237
USPC ................ 438/197, 478; 257/9, 77, E21.041, 257/E21.135
See application file for complete search history.

(56) References Cited

U.S. PATENT DOCUMENTS 7,605,081 B2 10/2009 Yang et al.
8,268,180 B2 * 9/2012 Arnold et al. .................... 216/56
(Continued)

FOREIGN PATENT DOCUMENTS

WO WO 2008/061224 A1 5/2008

OTHER PUBLICATIONS

Max C. Lemme, Tim J. Echtermeyer, Matthias Baus, and Heinrich Kurz, A Graphene Field-Effect Device, IEEE Electron Device Letters, vol. 28, No. 4 (Apr. 2007) p. 282.*
(Continued)

*Primary Examiner* — Matthew W Such
*Assistant Examiner* — Stephen C Smith
(74) *Attorney, Agent, or Firm* — Vista IP Law Group LLP (57) ABSTRACT

A graphene nanomesh includes a sheet of graphene having a plurality of periodically arranged apertures, wherein the plurality of apertures have a substantially uniform periodicity and substantially uniform neck width. The graphene nanomesh can open up a large band gap in a sheet of graphene to create a semiconducting thin film. The periodicity and neck width of the apertures formed in the graphene nanomesh may be tuned to alter the electrical properties of the graphene nanomesh. The graphene nanomesh is prepared with block copolymer lithography. Graphene nanomesh field-effect transistors (FETs) can support currents nearly 100 times greater than individual graphene nanoribbon devices and the on-off ratio, which is comparable with values achieved in nanoribbon devices, can be tuned by varying the neck width. The graphene nanomesh may also be incorporated into FET-type sensor devices.

47 Claims, 8 Drawing Sheets

(51) Int. Cl.
*H01L 29/786* (2006.01)
*B82Y 30/00* (2011.01)
*B82Y 40/00* (2011.01)
*C01B 31/04* (2006.01)
*G01N 27/414* (2006.01)

(52) U.S. Cl.
CPC ..... *C01B 31/0484* (2013.01); *H01L 29/66742* (2013.01); *H01L 29/78696* (2013.01); *G01N 27/4146* (2013.01); *G01N 27/4145* (2013.01)

(56) References Cited

U.S. PATENT DOCUMENTS

| 8,440,331 | B2* | 5/2013 | Liu | 428/828 |
|---|---|---|---|---|
| 2008/0073743 | A1 | 3/2008 | Alizadeh et al. | |
| 2009/0200646 | A1 | 8/2009 | Millward et al. | |
| 2010/0012176 | A1 | 1/2010 | Curtin et al. | |
| 2010/0025660 | A1* | 2/2010 | Jain et al. | 257/24 |
| 2010/0127312 | A1* | 5/2010 | Grebel et al. | 257/288 |

OTHER PUBLICATIONS

PCT International Search Report for PCT/US2011/023002, Applicant: The Regents of the University of California, Form PCT/ISA/210 and 220, dated Oct. 25, 2011(6pages).

PCT Written Opinion of the International Search Authority for PCT/US2011/023002, Applicant: The Regents of the University of California, Form PCT/ISA/237, dated Oct. 25, 2011 (6pages).

PCT International Preliminary Report on Patentability (Chapter I of the Patent Cooperation Treaty) for PCT/US2011/023002, Applicant: The Regents of the University of California, Form PCT/IB/326 and 373, dated Aug. 16, 2012 (6pages).

Bai, Jingwei et al., Graphene Nanomesh, Nature Nanotechnology, vol. 5, pp. 190-194, Mar. 2010, published online: Feb. 14, 2010.

Duan, Xiangfen, Assembled Semiconductor Nanowire Thin Films for High-Performance Flexible Macroelectronics, MRS Bulleting, vol. 32, pp. 134-141, Feb. 2007.

Jiao, Liying et al., Narrow graphene nanoribbons from carbon nanotubes, Nature, vol. 458, pp. 877-880, Apr. 16, 2009.

Li, Xuesong et al., Large-Area Synthesis of High-Quality and Uniform Graphene Films on Copper Foils, Science, vol. 324, pp. 1312-1314, Jun. 5, 2009.

Park, Sungjin et al., Chemical methods for the production of graphenes, Nature Nanotechnology, vol. 4, pp. 217-224, Apr. 2009.

Reina, Alfonso et al., Large Area Few-Layer Graphene Films on Arbitrary Substrates by Chemical Vapor Deposition, Nano Letters, vol. 9, No. 1, pp. 30-35, 2009.

Tung, Vincent C. et al., High-throughput solution processing of large-scale graphene, Nature Nanotechnology, vol. 4, pp. 25-29, Jan. 2009.

* cited by examiner

GRAPHENE NANOMESH AND METHOD OF MAKING THE SAME

RELATED APPLICATION

This Application is a U.S. National Stage filing under 35 U.S.C. §371 of International Application No. PCT/US2011/023002, filed Jan. 28, 2011, which claims priority to U.S. Provisional Patent Application No. 61/300,398 filed on Feb. 1, 2010. The above-noted Applications are incorporated by reference as if set forth fully herein. Priority is claimed pursuant to 35 U.S.C. §§371, 119 and any other applicable statute.

STATEMENT REGARDING FEDERALLY SPONSORED RESEARCH AND DEVELOPMENT

This invention was made with Government support under OD004342, awarded by the National Institutes of Health. The Government has certain rights in the invention.

FIELD OF THE INVENTION

The field of the invention generally relates graphene and, in particular, methods of making graphene nanomesh and devices incorporating graphene nanomesh.

BACKGROUND OF THE INVENTION

Graphene is the two-dimensional crystalline form of carbon made of a single layer of carbon atoms arranged in hexagons, like a honeycomb. Graphene has attracted considerable interest as a new electronic material for fundamental studies and potential applications in future electronics due to its exceptional electronic characteristics. The room temperature carrier mobility of graphene devices can reach 15,000 $cm^2/V \cdot s$ or higher, making it an attractive candidate for next generation electronics. However, two-dimensional graphene is a semi-metal with zero band gap and remains highly conductive even at the charge neutrality point, and therefore, cannot be used for field-effect transistors (FETs) at room temperature.

The formation of nanostructures with lateral quantum confinement can open up a finite band gap in graphene. In particular, graphene nanoribbons (GNRs) have been predicted to be semiconducting due to edge effects and the quantum confinement of electron wave functions in the transverse direction. Theoretical calculations have suggested that the band gap of GNRs scales inversely with their width, and a width in the sub 10 nanometer regime is required to create a sufficiently large band gap for room temperature transistor operation.

For example, a band gap of 0.67 eV (like Ge) requires a ribbon width of 2-3 nm. However, it is non-trivial to obtain GNRs in the sub 10 nm regime experimentally. Conventional electron beam (e-beam) lithography can produce GNRs of variable widths, and it has been demonstrated that the band gap of the GNRs indeed inversely scales with the width. However, the smallest GNR width that can be obtained using e-beam lithography is about 15-20 nm, which prevents this method from being used to obtain GNRs with a sufficiently large band gap for room temperature FETs.

Additionally, GNRs fabricated by e-beam lithography usually have a line edge roughness of 1-3 nm, which can adversely impact their electronic properties, and makes it practically impossible to obtain uniform GNRs in the sub 5 nm regime using conventional lithography. Interestingly, it has recently been shown that chemical exfoliation and sonication can produce GNRs with ultra-narrow widths down to 2-3 nanometers. See Jiao, L. Y., Zhang, L., Wang, X. R., Diankov, G. & Dai, H. J. Narrow Graphene Nanoribbons From Carbon Nanotubes, Nature 458, 877-880 (2009). Room temperature FETs have been demonstrated from these ultra-narrow GNRs. However, the GNRs obtained with this method came from a chance observation rather than through a specific fabrication process, and there is no clear pathway to rationally control the width of the resulting GNRs. Longitudinal unzipping of carbon nanotubes was also recently explored to produce GNRs around the 10 nm regime. In this regard, methods have been proposed to fabricate GNRs with controllable widths from 6-10 nm using chemical synthesized nanowires as etch masks. See Duan, X. Assembled semiconductor nanowire thin films for high-performance flexible macroelectronics. MRS Bulletin 32, 134-141 (2007). Using such GNRs as the semiconducting channel, room temperature FETs have been fabricated with on-off ratios of >100.

However, the devices made from GNRs often have limited driving current, transconductance or frequency response determined by the intrinsic properties of individual GNRs, which can severely limit the capability to rationally design and fabricate devices to meet specific circuit requirements. To ensure sufficiently large driving current or transconductance for high frequency circuits will require the high-density assembly of multiple uniform GNRs in parallel, which has not been achieved to date. Additionally, integration of nanoribbon devices into a useful circuit will also require large scale hierarchical assembly of nanoribbons into highly organized arrays over multiple length scales. These assembly requirements are highly elusive considering the limited success to date in related topics on the assembly of nanotubes and nanowires after more than ten years of intensive research.

SUMMARY

In one embodiment of the invention, a graphene nanomesh includes a sheet of graphene having a plurality of periodically arranged apertures, wherein the plurality of apertures have a substantially uniform periodicity and substantially uniform neck width. The periodicity of apertures may vary depending the particular application and use but generally is less than 50 nm. In other embodiments, the periodicity is less than 30 nm or even less than 10 nm. Similarly, the neck width of the apertures may vary depending on the particular application and use but generally is less than 30 nm. In other embodiments, the neck width is less than 10 nm or even less than 5 nm.

In another embodiment of the invention, a method of forming graphene nanomesh includes providing a sheet of graphene, forming a block copolymer thin film on the graphene, selectively removing a block copolymer domain from the thin film so as to form a mask containing a plurality of apertures in the thin film, and etching away regions of the graphene exposed by the mask so as to form a plurality of apertures in the sheet of graphene.

In one embodiment, the block copolymer poly(styrene-block-methyl methacrylate) P(S-b-MMA) is used but the method is also applicable to other block copolymers. The graphene nanomesh that is created may remain on the substrate or it may be lifted off where it may be stored in its pristine state. Alternatively, the graphene nanomesh may be transferred to another substrate.

In still another embodiment, the graphene nanomesh may be incorporated into a transistor device in which the graphene nanomesh forms the channel. The transistor may have a back gate electrode or, alternatively, a top gate electrode.

In yet another embodiment, the graphene nanomesh is used in a sensor. The sensor includes a source, a drain, a gate, and a channel region formed from a graphene nanomesh that includes a biomolecule immobilized to the surface of the graphene nanomesh, the biomolecule being configured to bind to a target.

In another aspect of the invention, a method of forming a graphene structure includes providing a sheet of graphene on a substrate and forming a thin layer of evaporated $SiO_x$ on the graphene. A thin film of block copolymer poly(styrene-block-methyl methacrylate) is formed on the graphene and is annealed. The annealed thin film of block copolymer poly (styrene-block-methyl methacrylate) is developed so as to form a polystyrene mask containing a plurality of apertures in the thin film. A $SiO_x$ hard mask is formed over the graphene by reactive ion etching followed by etching away exposed regions of the graphene with $O_2$ plasma so as to form a plurality of apertures in the sheet of graphene. The $SiO_x$ hard mask is removed by exposing the hard mask to hydrofluoric acid, thereby forming a graphene structure having a plurality of holes therein.

In still another embodiment, a graphene structure is disclosed that includes a sheet of graphene having an array of periodically arranged holes in the surface thereof.

DETAILED DESCRIPTION OF THE ILLUSTRATED EMBODIMENTS

Figure 1:
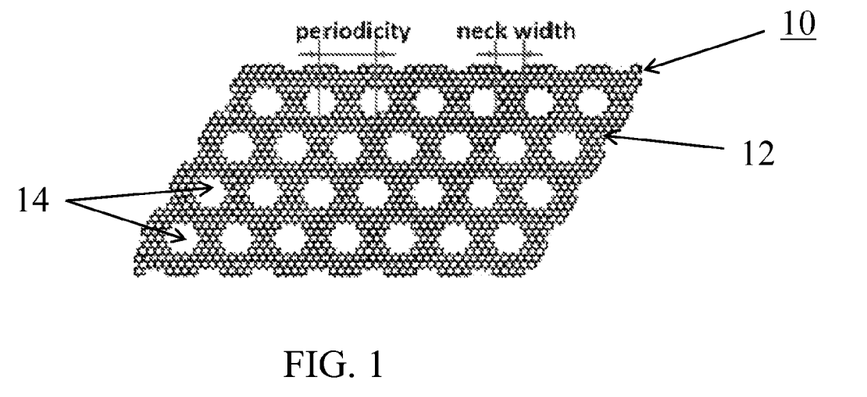
FIG. 1 illustrates a schematic illustration of graphene nanomesh.

FIG. 1 illustrates a schematic illustration of graphene nanomesh 10. The graphene nanomesh 10 includes a sheet 12 of graphene having a plurality of apertures 14 formed therein. The sheet 12 of graphene may have a single layer of graphene or, alternatively, several layers of graphene. The plurality of apertures 14 are periodically arranged throughout the sheet 12. The graphene nanomesh 10 has two structural parameters that affect the electrical properties of the sheet 12. The first structural parameter is the "periodicity" of the apertures 14 and is defined as the center-to-center distance between two neighboring apertures 14. The second structural parameter is the "neck width" of the apertures 14 and is defined as the smallest edge-to-edge distance between two neighboring apertures 14 in the graphene nanomesh 10. Both the periodicity and the neck width are illustrated in FIG. 1.

Periodicity and neck width define the basic structural information in the graphene nanomesh 10, and also fundamentally determines the electric properties of the graphene nanomesh 10. By controlling the neck width in the graphene nanomesh 10, one can effectively fine tune the degree of lateral quantum confinement and therefore engineer the size of the band gap and on-off ratio that can be achieved in a device that incorporations the graphene nanomesh 10. By controlling the periodicity, one can control the total lateral area of the interconnected graphene network that contributes to conducting current and therefore controls the driving current, transconductance and frequency response of the device. An additional structural parameter, the relative orientation of the lattice of apertures 14 formed in the graphene nanomesh 10 may also affect the electrical properties of the sheet.

Generally, the plurality of apertures 14 formed in the graphene nanomesh 10 have a substantially uniform periodicity over the entire sheet 12. Similarly, the plurality of apertures 14 formed in the graphene nanomesh 10 have a substantially uniform neck width. Generally, the standard deviation of both the periodicity and neck width is less than or equal to 2 nm.

Figure 2:
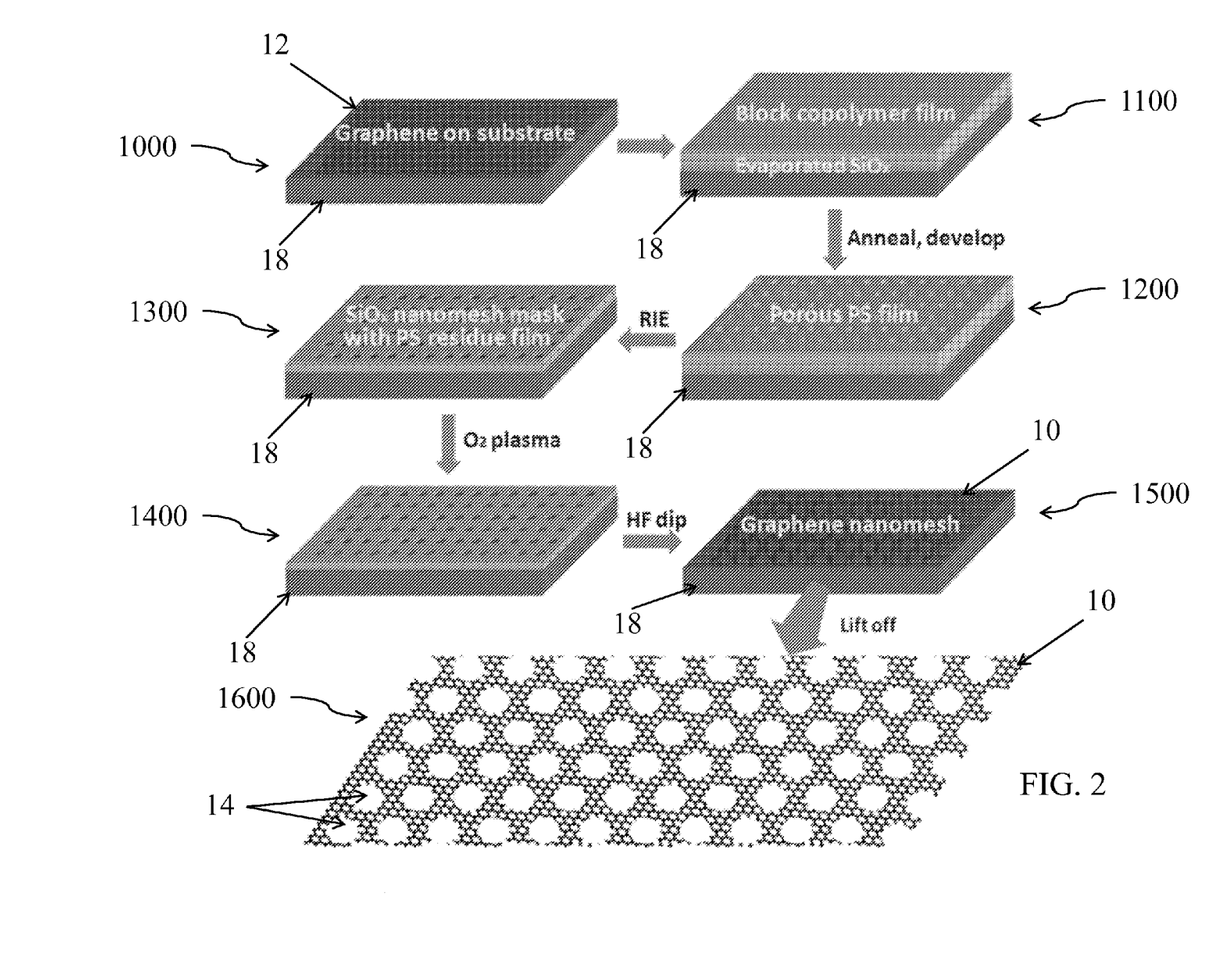
FIG. 2 illustrates one process of fabricating a graphene nanomesh.

FIG. 2 illustrates one process of fabricating a graphene nanomesh 10. Initially, in operation 1000 a sheet 12 of graphene is deposited or otherwise formed onto a substrate 18. The sheet 12 of graphene may be obtained by mechanically peeling a graphene sheet 12 from source of graphite. The peeled graphene sheet 12 is then transferred to the substrate 18. In one aspect, the sheet 12 of graphene is obtained using the so-called "Scotch tape" approach in which an adhesive tape is placed over a source of graphite and peeled off which causes the sheet 12 of graphene to be adhered to the adhesive tape. The sheet 12 of graphene is then transferred to the substrate 18. Residue from the adhesive tape may need to be removed which can be done by calcination at 300° C. in air to remove organic residues.

Alternative approaches may also be used to create the sheet 12 of graphene. For example, exfoliation or chemical vapor deposition techniques may be employed to create the sheet 12 of graphene. Such techniques are described in more detail in the following publications, which are incorporated by reference as if set forth fully herein. Park, S. et al., Chemical methods for the production of graphenes, Nature Nanotech, 4, 217-224 (2009); Tung, V. C. et al., High-throughput solution processing of large-scale graphene, Nature Nanotech, 4, 25-29 (2009); Li, X. et al. Large-area synthesis of high quality and uniform graphene films on copper foils, Science 324, 1312-1314 (2009); Reina, A. et al., Large area, few-layer graphene films on arbitrary substrates by chemical vapor deposition, Nano Lett., 9, 30-35 (2009).

In the method illustrated in FIG. 2, the sheet 12 of graphene was mechanically peeled using the Scotch tape method described above and transferred to a substrate 18 that comprised a highly doped p-type silicon wafer having a 300 nm thermal oxide coating. Next, as seen in operation 1100, a 10-nm $SiO_x$ thin film was evaporated onto sheet 12 of graphene using e-beam evaporator operated at $10^{-6}$ torr. This fresh oxide surface was functionalized with P(S-r-MMA) random copolymer (Polymer Source, Inc., Quebec, Canada: 11000, Mw/Mn: 1.15, styrene 55 mol %, functionalized α-hydroxyl and ω-tempo moiety) by spin coating a thin film from 1 wt % toluene solution. This film was annealed at 170° C. for 72 hours to anchor the polymer onto oxide surface through end hydroxyl group, and then rinsed with toluene to remove unanchored polymer.

Still referring to operation 1100, the block copolymer thin film was prepared on the neutralized surface by spin coating 1 wt % filtered polymer solution at 2500 rpm followed by annealing at 180° C. for 12 hours. The block copolymer thin film was formed using poly(styrene-block-methyl methacrylate), namely, P(S-b-MMA) with molecular weight of 77000 g $mol^{-1}$ (PS-PMMA: 55000-22000, Mw/Mn: 1.09) and 47700 g $mol^{-1}$ (PS-PMMA: 35500-12200, Mw/Mn: 1.04) purchased from Polymer Source, Inc. and dissolved in toluene. The block copolymer layer on the sheet 12 of graphene forms a thin film with cylindrically-shaped domains oriented normal or perpendicular to the surface. The thickness was determined to be 30-35 nm by atomic-force-microscopy (AFM) profile. The annealed film was exposed to 295 nm UV irradiation for 30 minutes under vacuum. The degraded PMMA cylindrical domains were removed by immersing in glacial acid for 20 minutes followed by extensive water rinsing. This leaves a porous PS matrix with cylindrical apertures to expose the underlying sheet 12 of graphene (obscured from view) as illustrated in operation 1200 of FIG. 2.

Referring now to operation 1300 of FIG. 2, to reach to the graphene layer, the P(S-r-MMA) random copolymer layer is removed by brief $O_2$ plasma etching (50 W, 4 mTorr) followed by $CHF_3$ based reactive ion etch (RIE) (50 W, 6 mTorr) to remove underlying silicon oxide (STS MESC Multiplex Advanced Oxide Etcher). The PS matrix layer is also partially removed during the RIE process due to the ion bombardment, leaving $SiO_x$ nanomesh hard mask on top of graphene (seen in operation 1300). The remaining PS mask and the exposed graphene area are then etched by another step of $O_2$ plasma etching process as illustrated in operation 1400. Operation 1500 illustrates a brief hydrofluoric (HF) acid dip which is used to remove the protecting $SiO_x$ mesh, leaving a graphene nanomesh 10 located on a $SiO_2$ substrate 18. Optionally, if desired, the free-standing graphene nanomesh 10 can be obtained by further etching the underlying $SiO_2$ using a lift off etch (e.g., HF etch) as shown in operation 1600.

In one embodiment, free-standing sheets 12 of graphene nanomesh 10 may be prepared by exfoliation of the graphene nanomesh 10 into solution to obtain bulk quantities. The bulk quantities of free-standing sheets 12 of graphene nanomesh 10 can be assembled onto various substrates to form high performance semiconducting thin forms. For example, lift-off polymer may be disposed on top of the graphene nanomesh 10 that remains after exfoliation or removal from the substrate. The graphene nanomesh 10 containing the polymer lift-off layer may then be transferred to another substrate 18. The substrate 18 may even be a flexible substrate (e.g., polymer) in which case the graphene nanomesh 10 is used for applications in flexible electronics.

Figure 3A:
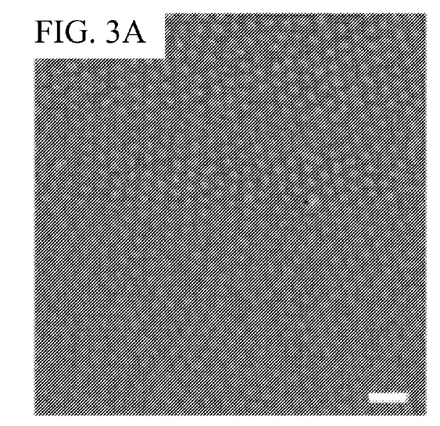
FIG. 3A illustrates an atomic force microscopy (AFM) image of the annealed P(S-b-MMA) thin film showing the cylindrical PMMA domains packed hexagonally within the PS matrix.
Figure 3B:
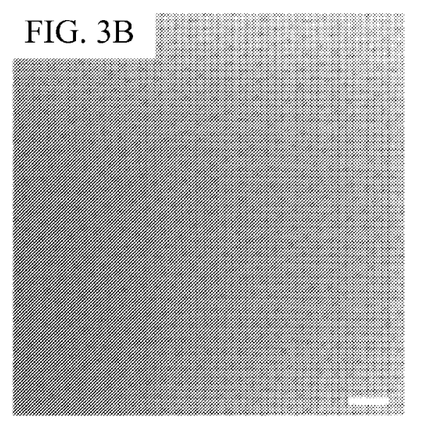
FIG. 3B illustrates a scanning electron microscopy (SEM) image of the microporous structure of PS matrix with hexagonally arranged apertures formed by the removed PMMA domains. The apertures vertically penetrate through the film.
Figure 3C:
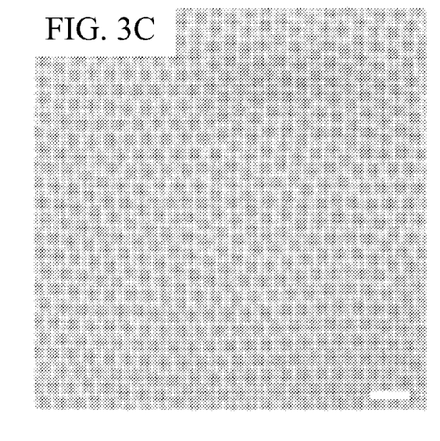
FIG. 3C illustrates a SEM image of the $SiO_x$ nanomesh mask after reactive ion etching with PS mask.
Figure 3D:
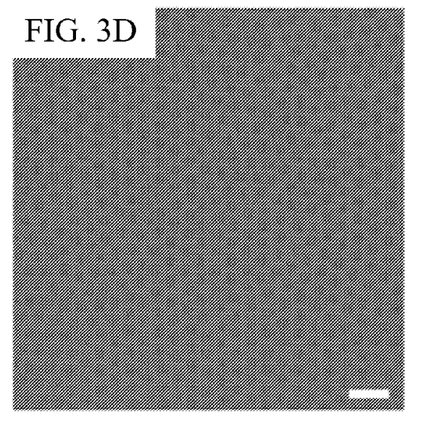
FIG. 3D illustrates a SEM image of graphene nanomesh structure after the top $SiO_x$ mesh mask has been removed. Scale bars indicate 100 nm.

FIG. 3A illustrates an atomic force microscopy (AFM) image of the annealed P(S-b-MMA) thin film showing the cylindrical PMMA domains packed hexagonally within the PS matrix. (AFM was done in tapping mode with a Veeco 5000). The domain center-to-center distance is approximately 39 nm by using P(S-b-MMA) with a molecular weight of 77,000 g mol-1 and a PS:PMMA volume ratio of 70:30. Changing the molecular weight while keeping the volume ratio constant can result in vertical aligned domains with variable center-to-center distance. Self-assembled hexagonal PMMA domains with center-to-center distance about 27 nm have been achieved by using copolymers with molecular weight of 47,700 g $mol^{-1}$. After UV exposure and glacial acid development to remove PMMA domains, a porous structure of PS matrix remained with hexagonally arranged apertures or nanoholes vertically penetrating through the film. FIG. 3B illustrates a scanning electron microscopy (SEM) image (SEM imaging was performed on a JEOL 6700F operated at 5 kV) of this structure. This corresponds to operation 1300 in FIG. 2. After the etching process drills into the underneath $SiO_x$ layer, this leaves a $SiO_x$ nanomesh mask on top of the graphene layer. AFM images of the $SiO_x$ nanomesh mask are illustrated in FIG. 3C. The resulting porous structure in oxide has slightly larger holes than that of PS template due to lateral etching of the PS mask. The oxide mask can be easily removed by briefly dipping the sample into HF solution and the hexagonal aperture 14 array in graphene can be seen under SEM in FIG. 3D.

To unambiguously determine the structure of the graphene nanomesh 10, transmission electron microscopy (TEM) studies were also conducted. TEM samples were prepared by spin coating a 300 nm thick layer of PMMA polymer resist onto the graphene nanomesh substrate and baked at 100° C. The PMMA-graphene nanomesh film 10 was then lifted off in HF solution and transferred onto the lacey film coated copper grid. After PMMA was removed by exposure to acetone vapor, the sample was characterized by JEOL 1200 operated at 80 kV.

Figure 4A:
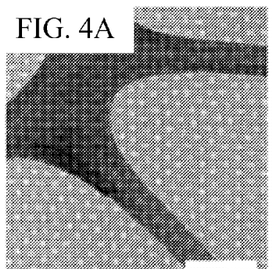
FIG. 4A illustrates a TEM image of a graphene nanomesh having a periodicity of 39 nm and neck width of 14.6 nm. The scale bar represents dimension of 200 nm.
Figure 4B:
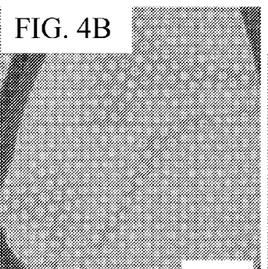
FIG. 4B illustrates a TEM image of a graphene nanomesh having a periodicity of 39 nm and neck width of 11.2 nm obtained with controlled over-etching. The scale bar represents dimension of 200 nm.
Figure 4C:
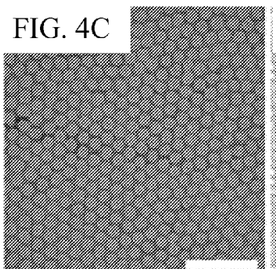
FIG. 4C illustrates a TEM image of a graphene nanomesh having a periodicity of 39 nm and neck width of 7.1 nm obtained with additional controlled over-etching. The scale bar represents dimension of 200 nm.
Figure 4D:
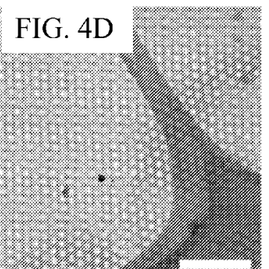
FIG. 4D illustrates a TEM image of a graphene nanomesh having a periodicity of 27 nm and neck width of 9.3 nm obtained with block copolymer (P(S-b-MMA)) of smaller molecular weight of 47700 g mol$^{-1}$. The scale bar represents dimension of 200 nm.
Figure 4E:
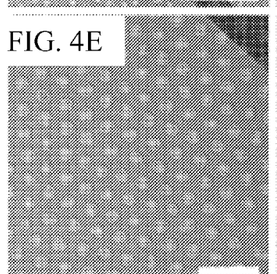
FIG. 4E illustrates a TEM image of a graphene nanomesh having a periodicity of 39 nm and neck width of 14.6 nm. The scale bar represents dimension of 100 nm.

FIGS. 4A-4H illustrate a series of TEM images of graphene nanomesh 10 with variable periodicities or neck widths. For better image contrast, most TEM images are taken from graphene nanomesh 10 having a relatively large thickness (5-10 nm), although images of graphene nanomesh 10 with one or a few layers of graphene have also been obtained but typically with lower contrast. The dark strips in the background of the images originate from the lacey carbon on TEM grids. TEM studies clearly show a graphene nanomesh 10 having a structure with nearly hexagonally arranged apertures 14, consistent with SEM studies. FIGS. 4A and 4E illustrate TEM images of a graphene nanomesh 10 obtained from a block copolymer (P(S-b-MMA) mask with molecular weight of 77000 g mol$^{-1}$, with an aperture periodicity of 39 nm and an average neck width of 14.6 nm. The apertures 14 observed here are slightly larger than the PMMA domains in the self-assembled block copolymer pattern due to slight over etching in the fabrication process. This nanomesh structure can be readily seen over many microns and apparently is only limited by the size of starting graphene fakes.

Figure 4F:
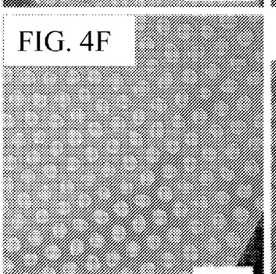
FIG. 4F illustrates a TEM image of a graphene nanomesh having a periodicity of 39 nm and neck width of 11.2 nm obtained with controlled over-etching. The scale bar represents dimension of 100 nm.
Figure 4G:
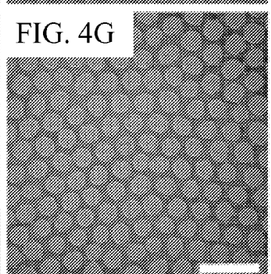
FIG. 4G illustrates a TEM image of a graphene nanomesh having a periodicity of 39 nm and neck width of 7.1 nm obtained with additional controlled over-etching. The scale bar represents dimension of 100 nm.
Figure 4H:
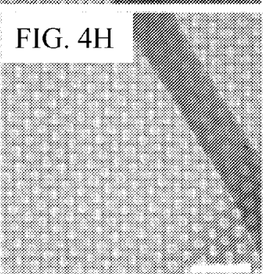
FIG. 4H illustrates a TEM image of a graphene nanomesh having a periodicity of 27 nm and neck width of 9.3 nm obtained with block copolymer (P(S-b-MMA)) of smaller molecular weight of 47700 g mol$^{-1}$. The scale bar represents dimension of 100 nm.

The fabrication process shows great versatility in controlling both the neck width and the periodicity independently. For example, the neck width can be tuned through controlled over-etching during the fabrication process. Over-etching involves etching of the block copolymer mask for an additional period of time (e.g., over etching the polymer resist during the $O_2$ plasma process). FIGS. 4B and 4F illustrate the TEM images of a graphene nanomesh 10 with the same periodicity of 39 nm, but a smaller average neck width of 11.2 nm through controlled lateral over-etch of the PS mask. FIGS. 4C and 4G illustrate a graphene nanomesh 10 with average neck width of 7.1 nm obtained with additional over-etching. Furthermore, it is also possible to tune the mesh periodicity and neck width by using block copolymer of different molecular weights. FIGS. 4D and 4H illustrate a much denser graphene nanomesh 10 having a smaller periodicity of 27 nm and average neck width of 9.3 nm obtained using smaller molecular weight of 477000 g mol$^{-1}$ block copolymer (P(S-b-MMA) thin film as the mask template.

Figure 5A:
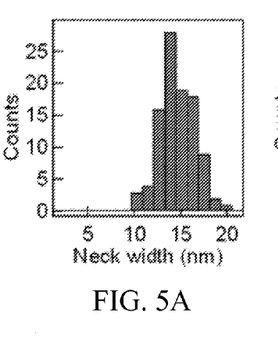
FIG. 5A illustrates a histogram of the graphene nanomesh 10 neck width corresponding to the graphene nanomesh illustrated in FIG. 4E. The average neck width is 14.6 nm with a standard deviation of 2.0 nm.
Figure 5B:
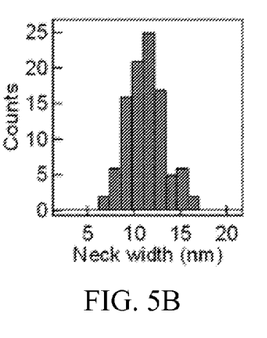
FIG. 5B illustrates a histogram of the graphene nanomesh 10 neck width corresponding to the graphene nanomesh illustrated in FIG. 4F. The average neck width is 11.2 nm with a standard deviation of 1.9 nm.
Figure 5C:
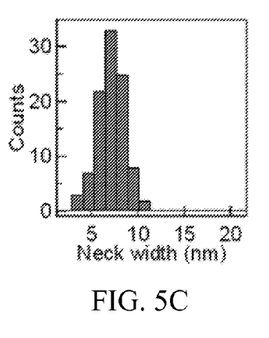
FIG. 5C illustrates a histogram of the graphene nanomesh 10 neck width corresponding to the graphene nanomesh illustrated in FIG. 4G. The average neck width is 7.1 nm with a standard deviation of 1.5 nm.
Figure 5D:
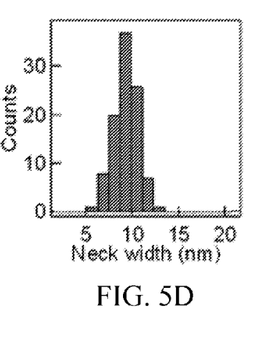
FIG. 5D illustrates a histogram of the graphene nanomesh 10 neck width corresponding to the graphene nanomesh illustrated in FIG. 4H. The average neck width is 9.3 nm with a standard deviation of 1.3 nm.

FIG. 5A illustrates a histogram of the graphene nanomesh 10 neck width corresponding to the graphene nanomesh illustrated in FIG. 4E. The average neck width is 14.6 nm with a standard deviation of 2.0 nm. FIG. 5B illustrates a histogram of the graphene nanomesh 10 neck width corresponding to the graphene nanomesh illustrated in FIG. 4F. The average neck width is 11.2 nm with a standard deviation of 1.9 nm. FIG. 5C illustrates a histogram of the graphene nanomesh 10 neck width corresponding to the graphene nanomesh 10 illustrated in FIG. 4G. The average neck width is 7.1 nm with a standard deviation of 1.5 nm. FIG. 5D illustrates a histogram of the graphene nanomesh 10 neck width corresponding to the graphene nanomesh 10 illustrated in FIG. 4H. The average neck width is 9.3 nm with a standard deviation of 1.3 nm. As seen above, as the average neck width decreases, the standard deviation also decreases.

The ability to control the periodicity and neck width of the graphene nanomesh 10 is important for controlling their electronic properties because charge transport properties are highly dependent on the width of the critical current pathway. The narrow neck width is needed to gain enough bandgap for sufficient gate response and on-off ratio in devices such as FETs, and denser mesh structure can enable higher current delivery. The method described herein is able to produce very small average neck widths and apertures 14 having very small periodicities. In one embodiment, the average neck width is less than 30 nm. In still other embodiments, the average neck width is less than 10 nm and, in still other embodiments, is less than 5 nm. The neck widths are substantially uniform across the graphene nanomesh 10. For instance, the standard deviation of neck widths may be less than 2 nm. The periodicity of the apertures 14 in the graphene nanomesh 10 may vary but is generally less than 50 nm. In other embodiments, the periodicity is less than 30 nm and in still other embodiments is less than 10 nm. The periodicity values are substantially uniform across the graphene nanomesh 10. For instance, the standard deviation of the periodicity is less than 2 nm.

Figure 6A:
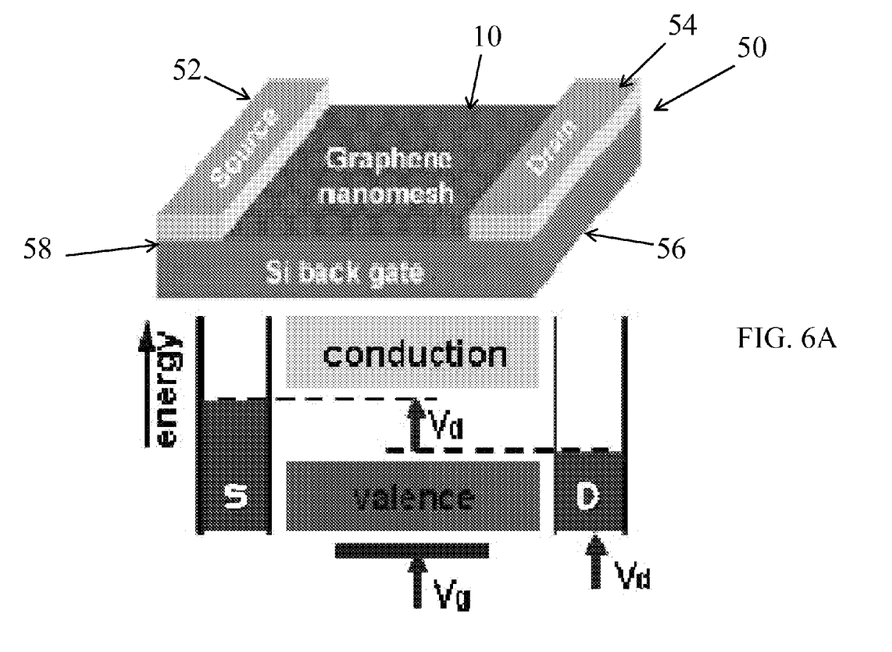
FIG. 6A illustrates a schematic of a graphene nanomesh-based FET device.
Figure 6B:
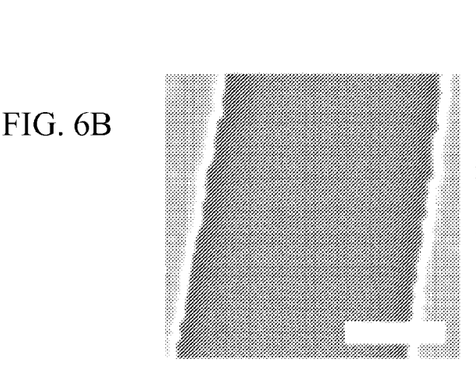
FIG. 6B illustrates an SEM image of the graphene nanomesh FET device 50 with a periodicity of 39 nm and neck width of 10 nm. The scale bar illustrates a dimension of 500 nm.

To investigate the electronic properties of the graphene nanomesh 10 structures, graphene nanomesh-based transistors were fabricated and electrical transport studies were conducted. A three terminal device transistor device 50 as illustrated in FIG. 6A was fabricated using the graphene nanomesh 10 as the semiconducting channel, e-beam evaporated Ti/Au pads as the source and drain contacts (52, 54), respectively, a highly doped p-type silicon substrate 56 as the back gate and a 300-nm thermal oxide ($SiO_2$) as the gate dielectric 58. FIG. 6B illustrates an SEM image of the graphene nanomesh FET device 50 with a periodicity of 39 nm and neck width of 10 nm. The scale bar illustrates a dimension of 500 nm.

Figure 6C:
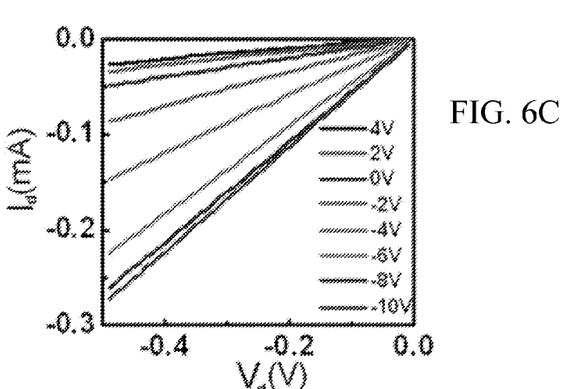
FIG. 6C is a graph illustrating Drain current ($I_d$) versus drain-source voltage ($V_d$) recorded at different gate voltages for a graphene nanomesh FET device with channel width of ~2 μm and channel length of ~1 μm.
Figure 6D:
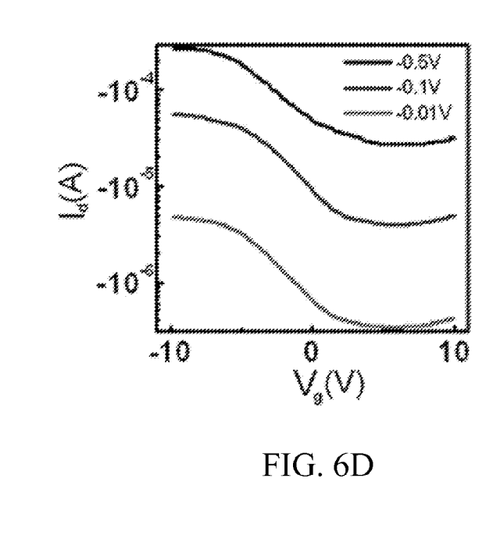
FIG. 6D illustrates the transfer characteristics of the graphene nanomesh FET device at different drain-source voltages ($V_d$=−10 mV, −100 mV and −500 mV). The ratio between $I_{on}$ to $I_{off}$ for this device was ~14 at $V_d$=−100 mV.
Figure 6E:
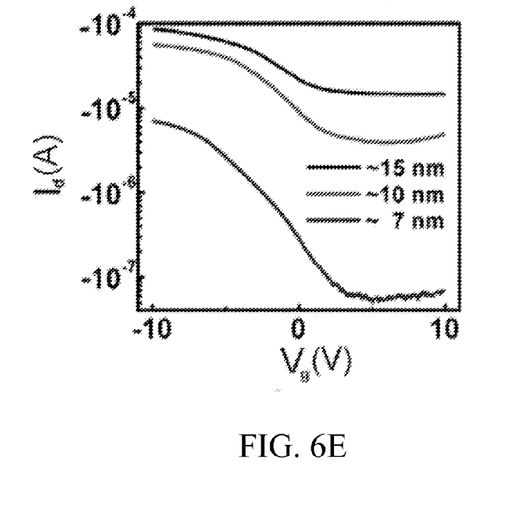
FIG. 6E illustrates the transfer characteristics of the graphene nanomesh FET device with a graphene nanomesh having varying neck widths of ~15 nm (device channel width 6.5 μm and length 3.6 μm), ~10 nm (channel width 2 μm and length 1 μm), and ~7 nm (channel width 3 μm and length 2.3 μm). Drain-source voltage ($V_d$=−100 mV).

FIGS. 6C and 6D illustrate the electrical transport characteristics of a typical graphene nanomesh transistor 50 with an estimated neck width of 10 nm. Electrical measurements were taken in ambient at room temperature and without removing top oxide layer. Drain current ($I_d$) versus drain-source voltage ($V_d$) at various gate voltages ($V_g$) for the graphene nanomesh transistor 50 show typical p-channel transistor behavior as best seen in FIG. 6C. The hole-doping observed in the graphene nanomesh transistor 50 is similar to GNR devices, and can be attributed to edge oxidation in the $O_2$ plasma process or physisorbed oxygen from the ambient and other species during the sample preparation steps. The plots of $I_d$ versus $V_g$ as illustrated in FIG. 6D at a constant $V_d$ values ($V_d$=−10 mV, −100 mV and −500 mV) show little current when the $V_g$ is more positive than a threshold voltage ($V_{th}$) of −0.6 V, and $I_d$ increases nearly linearly when the $V_g$ increases in the negative direction. The plot shows the device 50 has an on-state conductance as high as 550 μS at $V_g$=−10 V, which is comparable to an array of ~50-100 parallel GNR devices. The $I_d$-$V_g$ plots also show the device 50 has an on-off ratio greater than 10, which is comparable to GNR FETs with widths in the range of 10-15 nm. Importantly, the on-off ratio of the graphene nanomesh devices can be readily tuned by varying neck width. Additional studies have shown a smaller on-off ratio of six (6) for a graphene nanomesh device 50 with larger neck width (~15 nm), and higher on-off ratio of more than 100 for graphene nanomesh device with smaller neck width (~7 nm) as seen in FIG. 6E. This observation is consistent with GNR devices where the conduction band gap and on-off ratio is inversely proportional to the width of the critical current pathway. Similar to GNRs, the opening of the conduction band gap in the graphene nanomesh structure can be attributed to a combination of multiple factors including lateral quantum confinement and localization effect resulted from edge disorder such as variable edge roughness or absorbed species in oxygen plasma etching process.

The on-off ratio can be further increased upon additional shrinking the neck width of the graphene nanomesh 10. The smaller neck width, as explained herein, can be achieved by over etching the polymer resist. These studies clearly demonstrate the formation of a graphene nanomesh 10 can effectively enable a semiconductor thin film with neck-width tunable electronic properties.

It is important to compare the performance of the graphene nanomesh-based devices with that of bulk graphene or GNRs. The on-state conductivity for the nm and 7 nm graphene nanomesh devices are approximately 1-2 orders of magnitude lower than that of bulk graphene, but comparable to that of similar width GNRs, although the total drive current can be 50-100 times greater than the GNR devices given the larger device width of the graphene nanomesh devices. The on-off ratio for the graphene nanomesh device 50 is comparable to that of similar width GNRs with the highest on-off ratio observed in the 7 nm graphene nanomesh about 5-6 times larger than the largest on-off ratios reported in bulk graphene. It should be noted that it is usually much more challenging to obtain a high on-off ratio (e.g., >100) than a medium on/off ratio (e.g., ~10) in a graphene nanomesh-based device while maintaining a high on-state conductivity, since the high on-off ratio devices require to reduce the neck width by aggressive over etching that can lead to partial breakage of the graphene nanomesh current pathway. It is also important to recognize that the requirement to achieve a similar on-off ratio in a bigger graphene nanomesh-based device is much more stringent than in a smaller single graphene nanomesh-based device, as each conducting channel needs to be small enough to afford a large on-off ratio. The ability to achieve high on-off ratio and high current in the large graphene nanomesh-based devices described herein clearly highlights the relative uniformity of the current graphene nanomesh film.

In another alternative embodiment, graphene nanomesh may be prepared using self-assembled nanodots instead of block copolymer lithographic techniques as disclosed herein. In this embodiment, highly uniform nanodots are synthesized. The surface of the nanodots are then coated with polyhedral oligomeric silsesquioxanes (POSS) molecules through a ligand exchange process. The nanodots are then spin-coated onto graphene to obtain a self-assembled hexagonal array. The distance between the dots is tuned by the size of the POSS ligands and extra POSS ligands added in solution. Upon a 300° C. curing process, the POSS ligands turn into $SiO_x$ with hexagonally assembled nanodots embedded therein. Selective etching to remove the nanodots can render a $SiO_x$ nanomesh mask with the neck width controlled by the size of the surface coating molecules. Using such a $SiO_x$ nanomesh as a mask, graphene nanomesh 10 with a periodicity in the 3-5 nm regime can be formed.

In one embodiment, graphene nanomesh 10 has particular applications for highly sensitive chemical and biological sensors. First, the exceptionally high mobility in graphene means very high voltage (i.e., charge) sensitivity. Second, the highly interconnected GNR-like network that is formed by the graphene nanomesh 10 permits sufficient device current to allow a sufficient signal-to-noise ratio. Third, the existence of a large amount of edge states can enable facile chemical modification and attachment of specific receptor molecules or moieties for the detection of specific analytes that only bind to the receptors. Finally, graphene is chemically stable and can ensure good compatibility.

Figure 7:
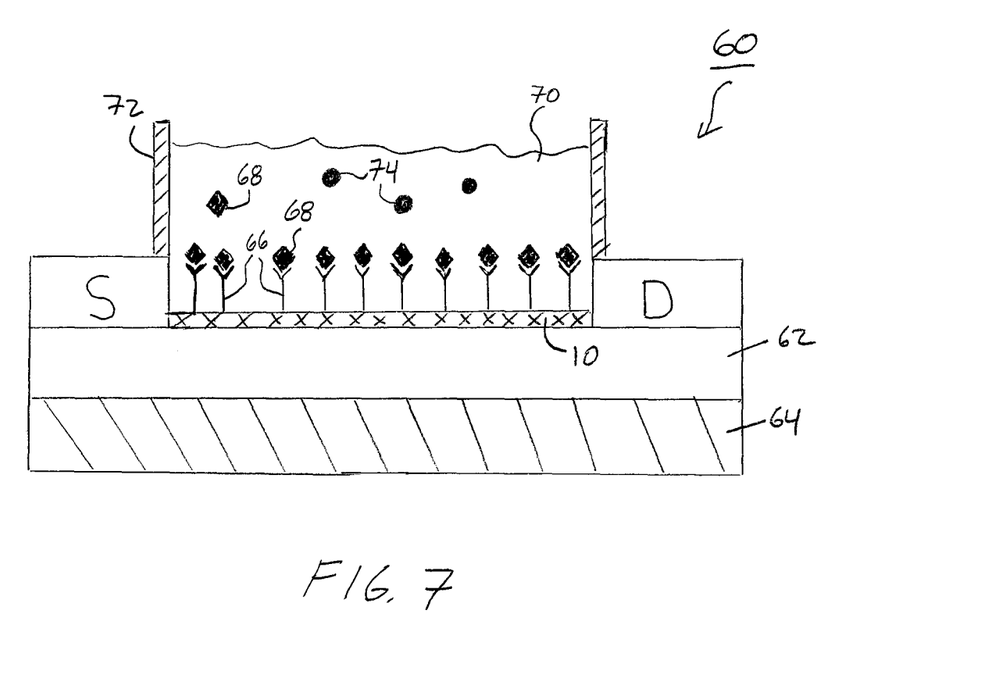
FIG. 7 schematically illustrates a sensor according to one embodiment.

FIG. 7 illustrates an embodiment of a sensor 60 that incorporates graphene nanomesh 10. In this embodiment, the sensor 60 is a FET-type conductivity sensor. The sensor 60 includes a source (S) and a drain (D), which may be formed by e-beam evaporating Ti/Au pads as the source-drain contacts. The sensor 60 also includes a channel region disposed between the source (S) and drain (D) that is formed from a graphene nanomesh 10 of the type described herein. The graphene nanomesh 10 is formed on for example a gate dielectric layer 62 which may include a thermal oxide ($SiO_x$). The dielectric layer 62 sits atop a substrate 64 which may include a highly doped p-type silicon substrate which acts as the back gate to the sensor device 60. The graphene nanomesh 10 includes an enzyme 66 or other biomolecule with binding affinity that is immobilized with respect to the graphene nanomesh 10. In one particular aspect of the invention, the enzyme 66 or other biomolecule may bind the circumferential edge regions of the apertures 14 formed in the graphene nanomesh 10. The enzyme 66 or biomolecule binds to a target 68 that is present within a sample 70 contained within a flow cell 72 or the like. The flow cell 72 may include a well or other reservoir into which the sample 70 is placed. Alternatively, the flow cell 72 may include a channel or the like (e.g., microfluidic channel) through which a sample 70 flows. In this regard, the sensor 60 may be used for real-time detection of sample 70 flowing by the sensor 60. The sample 70 may also contain other species 74 that do not bind to the enzyme 66 or biomolecule as illustrated in FIG. 7.

In operation, a gate voltage (V) is applied to the back gate 64 and the conductance (μS) of the graphene nanomesh 10 will change in response to binding of the target 68. The conductance may be measured using conventional off-sensor electronics known to those skilled in the art. The conductance of the graphene nanomesh 10 may change as a result of electrical charge distribution at or near the surface of the graphene nanomesh 10 or through localized chemical reactions that may affect the conductance of the underlying graphene nanomesh 10. For example, chemical reactions occurring at or near the surface may cause localized doping (e.g., increasing the number of holes) in the graphene nanomesh 10. The conductance may be measured as a function of time to detect the presence or absence of a target 68. In addition, calibration curves may be created at one or more applied gate voltages (V) that can differentially distinguish between different concentrations of the target.

In yet another embodiment, the graphene nanomesh 10 may be employed in the formation of a top-gated transistor 80. Top-gated transistors using high-k dielectrics such as $Al_2O_3$ of $HfO_2$ can significantly reduce switching voltage and really allow independently addressable device arrays and functional circuits. In one embodiment, graphene nanomesh 10 is integrated with high quality high-k dielectrics using free-standing dielectric nanoribbons. Nanoribbons can be synthesized at high temperature with nearly perfect crystalline structure, but manipulated and assembled at room temperature. This flexibility allows the integration of normally incompatible materials and processes and can enable unique functions in electronics or photonics.

Figure 8:
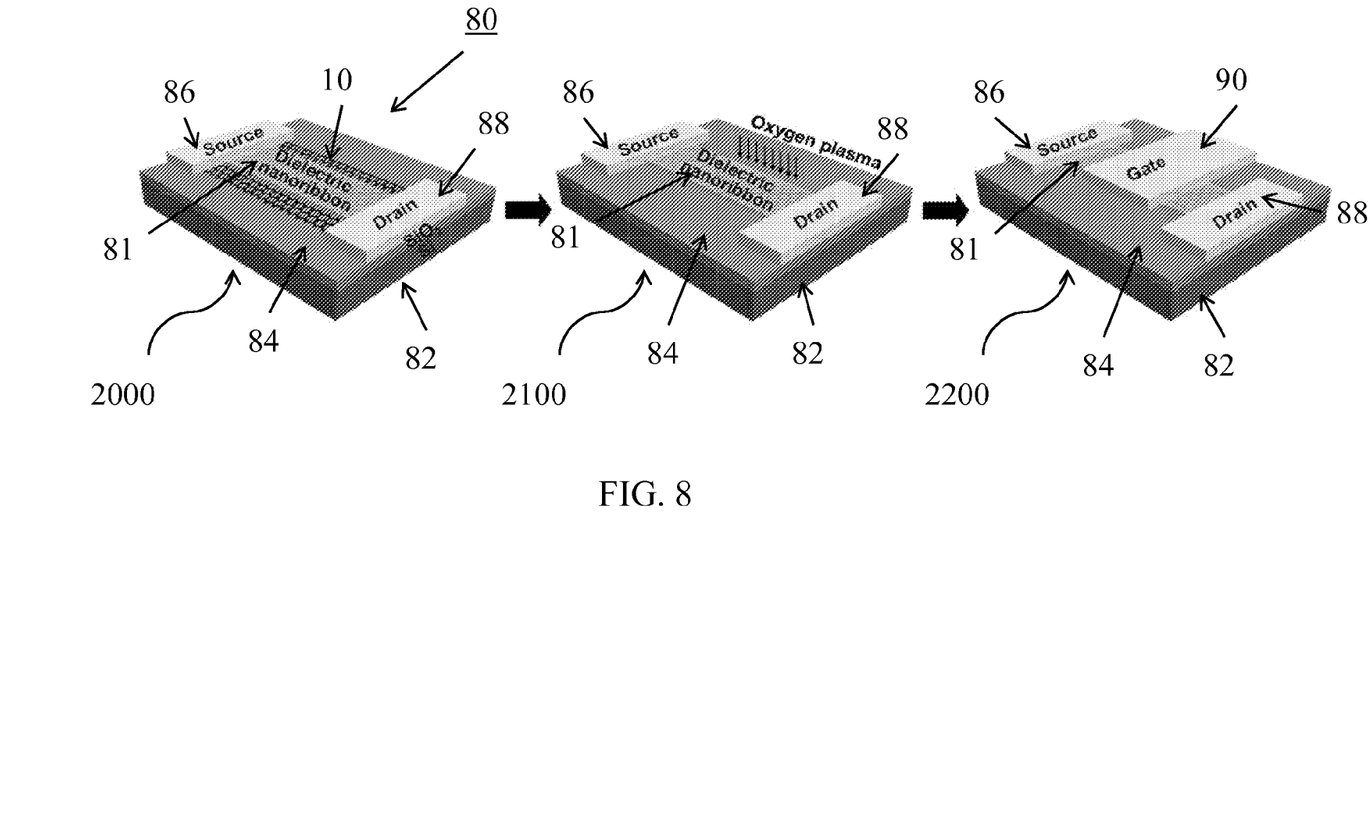
FIG. 8 illustrates a process for forming a top-gated graphene nanomesh transistor.

In this embodiment, $Al_2O_3$ is used as the high-k dielectric in a top-gated transistor. Specifically, high quality dielectric $Al_2O_3$ nanoribbons 81 are first synthesized and then transferred onto a channel comprising graphene nanomesh 10. The $Al_2O_3$ nanoribbons 81 act as the gate dielectric for the top-gated graphene transistor. This integration approach preserves the pristine nature of the graphene nanomesh 10 and allows high room temperature mobility.

FIG. 8 illustrates an exemplary fabrication process to obtain a top-gated transistor 80. A silicon substrate 82 is provided having a $SiO_2$ layer 84 formed thereon. A graphene nanomesh 10 layer forms the channel region of the transistor 80 formed between a source 86 and drain 88. The graphene nanomesh 10 may be interposed between the $SiO_2$ layer and the source 86 and drain 88.

Aluminum oxide ($Al_2O_3$) nanoribbons 81 may be synthesized through a physical vapor transport approach at 1400° C. To grow $Al_2O_3$ nanoribbons 81, aluminum, and nanometer-sized $Al_2O_3$ powders with a molar ratio of 4:1 may be used as the starting materials. A ceramic boat with the mixture is placed at the center of a horizontal tube furnace and an alumina piece is placed at the downstream end as the deposition substrate. The temperature can be raised to target temperature with a flow of 400 sccm Ar as the carrying gas. The temperature may be maintained for 1 hour and then naturally cooled to room temperature.

Referring to FIG. 8, in the operation 2000 $Al_2O_3$ nanoribbons 81 are aligned on top of the graphene nanomesh 10 using a physical dry transfer process. The overall process involves physical transfer of $Al_2O_3$ nanoribbons 81 directly from a $Al_2O_3$ nanoribbon growth substrate to a graphene nanomesh 10 substrate via contact printing. Specifically, a graphene nanomesh 10 device substrate is first firmly attached to a benchtop, and the $Al_2O_3$ nanoribbon growth substrate is placed upside down on top of the graphene substrate so that the $Al_2O_3$ nanoribbons 81 are in contact with the graphene. A gentle manual pressure is then applied from the top followed by slightly sliding the growth substrate. The $Al_2O_3$ nanoribbons 81 are aligned by sheer forces during the sliding process. The sliding process results in direct dry transfer of nanoribbons 81 from the growth substrate to the desired graphene nanomesh 10 substrate. The sample is then rinsed with isopropanol followed by nitrogen blow-dry, in which the capillary drying process near the $Al_2O_3$ nanoribbons can help the $Al_2O_3$ nanoribbons 81 to be firmly attached to the substrate surface.

After alignment of the $Al_2O_3$ nanoribbons 81 on the graphene nanomesh 10, e-beam lithography and metallization processes can be used to define the source 86 and drain 88 electrodes as illustrated in operation 2000. Oxygen plasma etch may then be used to remove the exposed graphene nanomesh 10, leaving only the graphene nanomesh 10 protected underneath the $Al_2O_3$ nanoribbon 81 and source electrode 86 and drain electrode 88 as illustrated in operation 2100. The top-gate electrode 90 may then be fabricated as illustrated in operation 2200.

A typical top-gate transistor device 80 consists of source electrode 86, drain electrode 88, and top-gate electrode (Ti/Au, 50 nm/50 nm) with $Al_2O_3$ nanoribbon 81 as the top-gate dielectric, a highly doped p-type silicon substrate 82 (<0.004 ohm·cm) as the back gate and a 300 nm thermal silicon oxide layer 84 as the back-gate dielectric.

While embodiments of the present invention have been shown and described, various modifications may be made without departing from the scope of the present invention. The invention, therefore, should not be limited, except to the following claims, and their equivalents.

What is claimed is:

1. A graphene nanomesh comprising:
   a sheet of graphene having a plurality of periodically arranged, cylindrically-shaped apertures, wherein the plurality of apertures have a substantially uniform periodicity and substantially uniform neck width.

2. The graphene nanomesh of claim 1, wherein the periodicity of the plurality of apertures is less than 50 nm.

3. The graphene nanomesh of claim 1, wherein the periodicity of the plurality of apertures is less than 30 nm.

4. The graphene nanomesh of claim 1, wherein the periodicity of the plurality of apertures is less than 10 nm.

5. The graphene nanomesh of claim 1, wherein the neck width is less than 30 nm.

6. The graphene nanomesh of claim 1, wherein the neck width is less than 10 nm.

7. The graphene nanomesh of claim 1, wherein the neck width is less than 5 nm.

8. The graphene nanomesh of claim 1, wherein the standard deviation of the periodicity is less than or equal to 2 nm.

9. The graphene nanomesh of claim 1, wherein the standard deviation of the neck width is less than 2 nm.

10. The graphene nanomesh of claim 1, further comprising a substrate secured to the graphene nanomesh.

11. The graphene nanomesh of claim 10, wherein the substrate comprises silicon oxide.

12. The graphene nanomesh of claim 10, wherein the substrate comprises a polymer.

13. A method of forming graphene nanomesh comprising:
    providing a sheet of graphene;
    forming a block copolymer thin film on the graphene;
    selectively removing a block copolymer domain from the thin film so as to form a mask containing a plurality of apertures in the thin film; and
    etching away regions of the graphene exposed by the mask so as to form a plurality of apertures in the sheet of graphene.

14. The method of claim 13, wherein the sheet of graphene is provided on a substrate.

15. The method of claim 13, wherein prior to forming a block copolymer thin film on the sheet of graphene, a silicon oxide film is formed thereon and functionalized with P(S-r-MMA) random copolymer.

16. The method of claim 13, wherein the block copolymer comprises poly(styrene-block-methyl methacrylate) (P(S-b-MMA)) block copolymer.

17. The method of claim 13, wherein etching away regions of the graphene exposed by the mask comprises reactive ion etching.

18. The method of claim 17, further comprising etching the graphene with $O_2$ plasma.

19. The method of claim 13, further comprising removing any remaining block copolymer.

20. The method of claim 15, further comprising removing the silicon oxide layer with hydrofluoric acid.

21. The method of claim 14, further comprising lifting the graphene nanomesh off the substrate.

22. The method of claim 13, wherein the plurality of apertures in the sheet of graphene have a substantially uniform periodicity and substantially uniform neck width.

23. The method of claim 22, wherein the periodicity of the plurality of apertures is less than 50 nm.

24. The method of claim 22, wherein the periodicity of the plurality of apertures is less than 30 nm.

25. The method of claim 22, wherein the periodicity of the plurality of apertures is less than 10 nm.

26. The method of claim 22, wherein the neck width is less than 30 nm.

27. The method of claim 22, wherein the neck width is less than 10 nm.

28. The method of claim 22, wherein the neck width is less than 5 nm.

29. The method of claim 22, wherein the standard deviation of the periodicity is less than or equal to 2 nm.

30. The method of claim 22, wherein the standard deviation of the neck width is less than 2 nm.

31. A transistor comprising a source electrode, a drain electrode, a gate electrode, and a channel region comprising a graphene nanomesh of claim 1.

32. The transistor of claim 31, wherein the gate electrode comprises a back gate electrode.

33. The transistor of claim 31, wherein the gate comprises a top gate electrode.

34. The transistor of claim 31, further comprising a dielectric nanoribbon interposed between the top gate electrode and the graphene nanomesh.

35. A sensor comprising a source electrode, a drain electrode, a gate electrode, and a channel region comprising a graphene nanomesh of claim 1, further comprising a biomolecule immobilized to the surface of the graphene nanomesh, the biomolecule configured to bind to a target.

36. The sensor of claim 35, further comprising a flow cell configured to hold a sample over the graphene nanomesh.

37. The sensor of claim 36, wherein the flow cell comprises a fluidic channel.

38. The sensor of claim 35, wherein the biomolecule comprises an enzyme.

39. A method of forming a graphene structure comprising:
providing a sheet of graphene on a substrate;
forming a thin layer of evaporated $SiO_x$ on the graphene;
forming a thin film of block copolymer poly(styrene-block-methyl methacrylate) on the graphene;
annealing the thin film of block copolymer poly(styrene-block-methyl methacrylate);
developing the thin film of block copolymer poly(styrene-block-methyl methacrylate) so as to form a polystyrene mask containing a plurality of apertures in the thin film;
forming a $SiO_x$ hard mask over the graphene by reactive ion etching;
etching away exposed regions of the graphene with $O_2$ plasma so as to form a plurality of apertures in the sheet of graphene; and
removing the $SiO_x$ hard mask by exposing the hard mask to hydrofluoric acid, thereby forming a graphene structure having a plurality of holes therein.

40. The method of claim 39, further comprising lifting off the graphene structure from the substrate.

41. The method of claim 39, wherein the plurality of holes in the graphene have average neck widths that are less than 15 nm.

42. The method of claim 39, wherein the plurality of holes in the graphene have average neck widths that are less than 12 nm.

43. The method of claim 39, wherein the plurality of holes in the graphene have average neck widths that are less than 10 nm.

44. The method of claim 39, wherein after the thin layer of evaporated $SiO_x$ is formed on the graphene, the surface is functionalized with P(S-r-MMA) random copolymer.

45. The graphene structure of claim 12, wherein the substrate is flexible.

46. The graphene structure of claim 14, wherein the substrate is flexible.

47. The graphene structure of claim 31, wherein the graphene nanomesh is disposed on a flexible substrate.

* * * * *